United States Patent
Calleja et al.

(10) Patent No.: US 10,100,340 B2
(45) Date of Patent: Oct. 16, 2018

(54) METHOD FOR CULTURING MICROALGAE OF THE AURANTIOCHYTRIUM GENUS IN A CULTURE MEDIUM WITHOUT CHLORIDE AND WITHOUT SODIUM FOR THE PRODUCTION OF DHA

(71) Applicant: FERMENTALG, Libourne (FR)

(72) Inventors: Pierre Calleja, Libourne (FR); Julien Pagliardini, Bordeaux (FR); Olivier Cagnac, Libourne (FR); Francois Godart, Vayres (FR)

(73) Assignee: FERMENTALG, Lib Ourne (FR)

( * ) Notice: Subject to any disclaimer, the term of this patent is extended or adjusted under 35 U.S.C. 154(b) by 73 days.

(21) Appl. No.: 15/301,091

(22) PCT Filed: Apr. 3, 2015

(86) PCT No.: PCT/FR2015/050881
§ 371 (c)(1),
(2) Date: Sep. 30, 2016

(87) PCT Pub. No.: WO2015/150716
PCT Pub. Date: Oct. 8, 2015

(65) Prior Publication Data
US 2017/0016036 A1 Jan. 19, 2017

(30) Foreign Application Priority Data
Apr. 3, 2014 (FR) .................... 14 52960

(51) Int. Cl.
| | | |
|---|---|---|
| *C12N 1/12* | (2006.01) | |
| *C12P 7/64* | (2006.01) | |
| *A23D 9/00* | (2006.01) | |
| *C11B 1/10* | (2006.01) | |
| *A23K 20/158* | (2016.01) | |
| *A23K 50/80* | (2016.01) | |
| *A23L 33/115* | (2016.01) | |

(52) U.S. Cl.
CPC .............. *C12P 7/6427* (2013.01); *A23D 9/00* (2013.01); *A23K 20/158* (2016.05); *A23K 50/80* (2016.05); *A23L 33/115* (2016.08); *C11B 1/10* (2013.01); *C12N 1/12* (2013.01)

(58) Field of Classification Search
CPC .............. C12P 7/64; C12P 7/6427; C12N 1/12
See application file for complete search history.

(56) References Cited

U.S. PATENT DOCUMENTS

| | | |
|---|---|---|
| 5,518,918 A | 5/1996 | Barclay |
| 6,410,281 B1 | 6/2002 | Barclay |
| 8,900,831 B2 | 12/2014 | Rusing et al. |
| 2007/0054384 A1 | 3/2007 | Rusing et al. |

FOREIGN PATENT DOCUMENTS

WO 2005/035775 A1 4/2005

OTHER PUBLICATIONS

Find grind sea salt amounts converter. 2018. On the web at convert-to.com/675/fine-sea-salt-conversion-and-typical-analysis.html.*
Hong et al. 2011; Production of lipids containing high levels of docosahexaenoic acid by a newly isolated microalga, *Aurantiochytrium* sp. KRS101. Applied Biochemicatry and Biotechnology. 164: 1468-1480.*
Kim et al. 2013; online Nov. 5, 2012; A novel fed-batch process based on the biology of *Aurantiochytrium* sp. KRS101 for the production of biodiesel and docosahexaenoic acid. Biosource Technology 135: 269-274.*
Yokoyama, R. et al. : "Taxonomic rearrangement of the genus Schizochytrium sensu lato based on morphology, chemotaxonomical characteristics and 18S rRNA gene phylogeny (Thraustochytriaceae, Labyrinthulomycetes, stramenopiles): emendation for Schizochytrium and erection of Aurantiochytrium and Oblongichytrium gen", Mycoscience, vol. 48, Nov. 2007 (Nov. 1, 2007), pp. 199-211.
Suleeporn Kitcha et al: Screening of Oleaginous Yeasts and Optimization for Lipid Production Using Crude Glycerol as a Carbon Source, Energy Procedia, vol. 9, 2011, pp. 274-282, XP028105725, ISSN: 1876-6102, DOI: 10.1016/J.EGYPRO.2011.09.029 [retrieved on Nov. 7, 2011] abstract p. 276, paragraph 3 p. 278, paragraph 1-4.
Ahmad et al.: "Growth optimization of thraustochytrid strain 12B for the commercial production of docosahexaenoic acid", Food Science and Biotechnology, vol. 22, No. 51, Feb. 1, 2013, pp. 53-58, XP055143597, ISSN: 1226-7708, p. 53, right-hand column, last paragraph—p. 54, left-hand column, paragraph 2 p. 54, right-land column, last paragraph p. 56, left-hand column, last paragraph—right-hand column, paragraph 1.
Shabala et al.: "Thraustochytrids can be grown in low-salt media without affecting PUFA production", Marine Biotechnology, vol. 15, 2013, pp. 437-444, ISSN: 1436-2228.
International Search Report, dated Dec. 23, 2015, from corresponding PCT application.

* cited by examiner

*Primary Examiner* — Karen Cochrane Carlson
(74) *Attorney, Agent, or Firm* — Young & Thompson (57) ABSTRACT

A method for culturing a protist of the *Aurantiochytrium mangrovei* genus. The genus is characterized genetically and by virtue of the lipid profile thereof. The method makes it possible to obtain a high biomass yield and a lipid, and more particularly docosahexaenoic acid (DHA), enrichment of the protists thus cultured. The development of a culture medium allows the production, at high cell density, of a DHA-rich protest of the *Aurantiochytrium mangrovei* genus. The medium is chemically defined at low sodium ion ($Na^+$) and chloride ion ($Cl^-$) content.

14 Claims, 4 Drawing Sheets
Specification includes a Sequence Listing.

SEQUENCE LISTING

<160> NUMBER OF SEQ ID NOS: 4

<210> SEQ ID NO 1
<211> LENGTH: 1210
<212> TYPE: DNA
<213> ORGANISM: Aurantiochytrium Mangrovei CCAP 4062/1

<400> SEQUENCE: 1

```
aagcatatgc taaagttgtt gcagttaaaa agctcgtagt tgaatttctg gcatgggcga      60
ccggtgcttt ccctgaatgg ggattgattg tctgcgttgc cttggccatc tttctcatgc     120
tattttggta tgagatcttt cactgtaatc aaagcagagt gttccaagca ggtcgtatga     180
```

```
ccggtatgtt tattatggga tgataagata ggacttgggt gctattttgt tggtttgcac    240
gcctgagtaa tggttaatag aacagttgg gggtattcgt atttaggagc tagaggtgaa    300
attcttggat ttccgaaaga cgaactagag cgaaggcatt taccaagcat gttttcatta    360
atcaagaacg aaagtctggg gatcgaagat gattagatac catcgtagtc tagaccgtaa    420
acgatgccga cttgcgattg ttgggtgctt tatacatggg cctcagcagc agcacatgag    480
aaatcaaagt ctttgggttc cggggggagt atggtcgcaa ggctgaaact taaaggaatt    540
gacggaaggg caccaccagg agtggagcct gcggcttaat ttgactcaac acgggaaaac    600
ttaccaggtc cagacatagg taggattgac agattgagag ctctttcatg attctatggg    660
tggtggtgca tggccgttct tagttggtgg agtgatttgt ctggttaatt ccgttaacga    720
acgagacctc ggcctactaa atagtgcgtg gtatggcaac atagtgcgtt tttacttctt    780
agagggacat gtccggttta cgggcaggaa gttcgaggca ataacaggtc tgtgatgccc    840
ttagatgttc tgggccgcac gcgcgctaca ctgatgggtt catcgggttt taatttcaat    900
ttttggaatt gagtgcttgg tcggaaggcc tgctaatcc ttggaacgct catcgtgctg    960
gggctagatt tttgcaatta ttaatctcca acgaggaatt cctagtaaac gcaagtcatc   1020
agcttgcatt gaatacgtcc ctgcccttg tacacaccgc ccgtcgcacc taccgattga   1080
acggtccgat gaaaccatgg gatgtttctg ttttggattca tttttggaca gaggcagaac   1140
tcgggtgaat cttattgttt agaggaaggt gaagtcgtaa caaggtttcc gtaggtgaac   1200
ctgcagaagg                                                        1210
```

<210> SEQ ID NO 2
<211> LENGTH: 952
<212> TYPE: DNA
<213> ORGANISM: Aurantiochytrium Mangrovei CCAP 4062/1
<220> FEATURE:
<221> NAME/KEY: misc_feature
<222> LOCATION: (918)..(918)
<223> OTHER INFORMATION: unknown

<400> SEQUENCE: 2

```
ttgtcggccg ccccaagcac cccggtatca tggttggtat ggaccagaag gacgcctatg     60
tcggtgatga ggcccagtcc aagcgtggtg tcctcaccct caagtacccc attgagcacg    120
gtatcgtgac caactgggac gacatggaga agatctggca ccacaccttc tacaacgagc    180
tccgcgttgc ccccgaggag cacccccgttc tcctcaccga ggccccccctc aaccccaagg    240 ccaaccgtga gcgcatgacc cagatcatgt tcgagacctt caacgtgccc gccatgtacg    300
tcaacatcca ggccgttctc tccctctacg cctctggtcg taccaccggt gccgtcctcg    360
actctggtga tggtgtcacc cacaccgtcc ccatctacga gggttacgct ctcccgcacg    420
ccgttctccg tatcgatctt gccggccgtg acctcaccga ctacatgatg aagatcctca    480
ccgagcgtgg ctactccttc accaccaccg ccgagcgcga aattgtccgt gacatcaagg    540
agaagctcgc ctacgtcgcc caggacttcg acgaggagat gcgcctcgcc gccgagtcct    600
ccgccctcga gaagtcctac gagcttccgg acggtaacgt catcaccatc ggcaacgagc    660
gcttccgctg ccccgaggtt ctcttccagc cgtccttcat cggcaaggag gcccagggtg    720
tccacgacac catgttccag accatcatga gtgtgacgt cgatatccgc aaggacctct    780
acgccaacat cgtcatgtct ggtggctcca ccatgtacga gggtctcgcc gctcgtctcg    840
agaaggagat gatcgccctt gccccctcca ccatgaagat caaggtcgtc gccccccctg    900
agcgcaagta ctccgtgngg atcggtggct ccattcttgc ctccctctcc ac            952
```

```
<210> SEQ ID NO 3
<211> LENGTH: 828
<212> TYPE: DNA
<213> ORGANISM: Aurantiocytrium Mangrovei CCAP 4062/1
<220> FEATURE:
<221> NAME/KEY: misc_feature
<222> LOCATION: (45)..(49)
<223> OTHER INFORMATION: unknown
<220> FEATURE:
<221> NAME/KEY: misc_feature
<222> LOCATION: (554)..(554)
<223> OTHER INFORMATION: unknown
<220> FEATURE:
<221> NAME/KEY: misc_feature
<222> LOCATION: (643)..(643)
<223> OTHER INFORMATION: unknown
<220> FEATURE:
<221> NAME/KEY: misc_feature
<222> LOCATION: (692)..(692)
<223> OTHER INFORMATION: unknown
<220> FEATURE:
<221> NAME/KEY: misc_feature
<222> LOCATION: (704)..(704)
<223> OTHER INFORMATION: unknown
<220> FEATURE:
<221> NAME/KEY: misc_feature
<222> LOCATION: (707)..(707)
<223> OTHER INFORMATION: unknown
<220> FEATURE:
<221> NAME/KEY: misc_feature
<222> LOCATION: (719)..(719)
<223> OTHER INFORMATION: unknown
<220> FEATURE:
<221> NAME/KEY: misc_feature
<222> LOCATION: (723)..(724)
<223> OTHER INFORMATION: unknown
<220> FEATURE:
<221> NAME/KEY: misc_feature
<222> LOCATION: (733)..(733)
<223> OTHER INFORMATION: unknown
<220> FEATURE:
<221> NAME/KEY: misc_feature
<222> LOCATION: (766)..(766)
<223> OTHER INFORMATION: unknown
<220> FEATURE:
<221> NAME/KEY: misc_feature
<222> LOCATION: (769)..(769)
<223> OTHER INFORMATION: unknown
<220> FEATURE:
<221> NAME/KEY: misc_feature
<222> LOCATION: (777)..(777)
<223> OTHER INFORMATION: unknown
<220> FEATURE:
<221> NAME/KEY: misc_feature
<222> LOCATION: (786)..(786)
<223> OTHER INFORMATION: unknown
<220> FEATURE:
<221> NAME/KEY: misc_feature
<222> LOCATION: (788)..(788)
<223> OTHER INFORMATION: unknown
<220> FEATURE:
<221> NAME/KEY: misc_feature
<222> LOCATION: (791)..(791)
<223> OTHER INFORMATION: unknown
<220> FEATURE:
<221> NAME/KEY: misc_feature
<222> LOCATION: (795)..(795)
<223> OTHER INFORMATION: unknown
<220> FEATURE:
<221> NAME/KEY: misc_feature
<222> LOCATION: (805)..(805)
<223> OTHER INFORMATION: unknown

<400> SEQUENCE: 3
tctcatccat accctcacca gtgtaccagt gaaggaaggc cttannnnng aacatgctgg      60
tgaactgctc agaaacacgc ttgaacatct cctggacggc ggtggtgtta ccgacaaagg     120
```

```
                                                    -continued tacaagacat cttgagaccc ttgggggga tgtcacagac agaggacttg atgttgttgg      180
ggatccactc aacaaagtag ctcgagttct tgttctgaac gttgagcatc tgctcgtcaa    240
cctccttggt ggacatgcgg ccacggaaga gggtggtggc agtgaggtag cgaccgtggc    300
ggggatcggc ggcgcacatc atgttcttgg catcgaaggc ctgctgggtg agctcgggaa    360
cggtgagagc acggtactgc tgggagccac gggaggtgag gggggagaag ccaatcatga    420
agaagtgaag acggggaag ggaatcaagt tcacagcgag cttacggagg tcagagttga     480
gctgaccagg gaagcgaagg cagcaagtgc agccagacat ggcagcgcac acaaggtggt    540
tgaggtcacc gtangtgggg gtggtgagct tgagggtgcg gaagcaaata tcgtagaggg    600
cctcgttatc gagaaccatg acctcatcag cgttctcaac aanctggtgg acagagagag    660
tggcgttgta aggctcgacg acggtatcag anaccttggg ggangnaca atagagaang    720 tanncatgat acngtcgggg tactcctcac ggatcttgct gatcanganc gtaccontac    780 cagatncngg naccnccacc gaggnagtgg gtgatctgga agccctgg                 828

<210> SEQ ID NO 4
<211> LENGTH: 879
<212> TYPE: DNA
<213> ORGANISM: Aurantiochytrium Mangrovei CCAP 4062-1

<400> SEQUENCE: 4
tcccaggccg atgttgccgt tctcgtcatt gactcttccc agggtggttt cgaggccggt     60
atcgccaagg atggccagac tcgtgagcac gctctcctcg ccttcaccct cggtatccag    120
cagatcatcg tcgccgtcaa caagatggac gacaagacca ccatgtactc tgaggcccgc    180
ttcaacgaga tcgtcaacga ggtttccgcc tacctcgcca aggtcggctt caagcccaag    240
aagatcaagt tcgtccccat ctccggctgg gctggtgaca acatgatcga gaagtcctcc    300
aacatgccct ggtacaaggg cccctacctt ctcgaggccc tcgacaacat caagcccccc    360
aagcgcccca tcgacaagcc tctccgtctt cccctccagg atgtgtacaa gatcggtggt    420
atcggaacgg tccccgtcgg ccgtgtcgag accggtgtca tcaagcccgg tatgaccgcc    480
tactttgccc ccaccggtgt gcagactgag gtcaagtccg tcgagatgca ccacgagtcc    540
atccccgagg ccaccccgg tgacaacgtt ggcttcaacg tcaagaacgt ttccgtcaag     600
gacatcaagc gcggtaacgt ctgtggtgat gccaagaacg accctccccg tggcgccaac    660
tccttcctcg cccaggttat cgtcatgggc caccccggtg agatccgcgc tggctacgca    720
ccagtcctcg attgccacac cgcccacatt gcctgcaagt tcgccgagat ccagaacaag    780
atggaccgtc gttccggtaa gatccttgag gatgccccca agttcatcaa gtccggtgac    840
tccgccatgg tcaagatgat cccctccaag aagatgtgc                           879
```

METHOD FOR CULTURING MICROALGAE OF THE AURANTIOCHYTRIUM GENUS IN A CULTURE MEDIUM WITHOUT CHLORIDE AND WITHOUT SODIUM FOR THE PRODUCTION OF DHA

The invention relates to a method for culturing cells of Thraustochytrids of the genus *Aurantiochytrium mangrovei*. The method makes it possible to obtain a high yield of biomass and an enrichment of the protists thus cultured in lipids and more particularly in docosahexaenoic acid (DHA). The invention relates to the development of a culture method which allows the high cell-density production of DHA-rich Thraustochytrids on chemically defined medium having a low content of sodium ions ($Na^+$) and of chloride ions ($Cl^-$).

The invention concerns only Thraustochytrids belonging to the genus *Aurantiochytrium*. This genus is delimited by a genetic, metabolic and physiological characterization.

The culture method, by which the cells are cultured with no significant addition of sodium ions ($Na^+$) or chloride ions ($Cl^-$), allows the high cell-density production—about 125 to 140 g/L of dry matter—of *Aurantiochytrium mangrovei*. This biomass is DHA-rich, with a level of 15 to 20 g/L of culture, preferably 20 to 25 g/L of culture, or even 25 to 30 g/L of culture.

Very small amounts of sodium chloride are present in the culture medium needed for this method, specifically very small amounts of chloride ions ($Cl^-$) and sodium ions ($Na^+$). Thus, in the culture medium, there is less than 1 g/L, preferably less than 0.5 g/L, more preferentially less than 0.2 g/L of chloride ions, and less than 100 mg/L, preferably less than 50 mg/L and more preferentially less than 6 mg/L of sodium ions ($Na^+$). This makes it possible to avoid the extra investment expenditures needed for equipment in contact with the medium and to reduce substantially the cost of treating effluents, avoid the disadvantages associated with the presence of chloride salt or sodium salt in the biomass, and reduce the cost of the medium by reducing the inputs (products added to the culture to improve the yield).

Preamble

Protists are currently the subject of numerous industrial projects because certain species are able to accumulate or secrete large amounts of lipids, in particular polyunsaturated fatty acids.

Among polyunsaturated fatty acids, certain highly unsaturated fatty acids (HUFAs) of the omega-3 series (PUFA-ω3), particularly eicosapentaenoic acid (EPA or C20:5 ω3) and docosahexaenoic acid (DHA or C22:6 ω3), and of the omega-6 series (PUFA-ω6), particularly arachidonic acid (ARA or AA or eicosatetraenoic acid C20:4 ω6), have a recognized nutritional importance and a strong potential in terms of therapeutic applications.

Regarded as an essential nutrient, DHA is necessary to the normal functional development of cells, and plays a crucial role in various biochemical processes and functions. It is essential to the development of the central nervous system and to retinal function, by incorporation in cell membranes, and plays a key role in the acquisition and the satisfactory maintenance of mechanisms involved in vision and memory.

Thraustochytrids, particularly *Aurantiochytrium*, are known to produce DHA when cultured heterotrophically [W. K. Hong et al. (2011); Production of lipids containing high levels of docosahexaenoic acid by a newly isolated microalga, *Aurantiochytrium* sp. KRS101. *Appl. Biochem. Biotechnol.*: 164(8):1468-80]. *Aurantiochytrium* is also known to produce carotenoids, such as astaxanthin, zeaxanthin, canthaxanthin, echinenone, beta-carotene and phoenicoxanthin [Yokoyama, R, Honda, D. (2007) Taxonomic rearrangement of the genus *Schizochytrium* sensu lato based on morphology, chemotaxonomic characteristics, and 18S rRNA gene phylogeny (Thraustochytriaceae, Labyrinthulomycetes): emendation for *Schizochytrium* and erection of *Aurantiochytrium* and *Oblongichytrium* gen. nov.; *Mycoscience*, Vol. 48, pp. 199-211].

To implement the production of fatty acids by protists on an industrial scale, several factors must be taken into account to make the production profitable. Among these factors, mention may be made of:

- the costs of raw materials and equipment (the purchase or lease and the maintenance thereof), as well as labor;
- the technical requirements of the production: for example, the number and technical difficulty of the preculture and culture steps, the online monitoring of the cultures, and the steps for treating the biomass derived from the culture in order to valorize the product;
- the treatment of effluents resulting from the culture.

The culture media currently used to culture protists of the Thraustochytrids family heterotrophically or mixotrophically contain significant amounts of salt, particularly sodium chloride. By way of example, mention may be made of the culture medium ATCC Medium No. 790 (11 g/L $Na^+$ and 19 g/L $Cl^-$).

The use of sodium chloride (NaCl) for culturing marine protists of the Thraustochytrids family in methods for producing oil and/or other molecules of interest involves large extra expenditures in terms of investment and effluent treatment and limits the valorization of the coproducts.

Indeed, chloride ions cause a degradation of stainless steel, a material used in the manufacture of fermentors, tools for preparing and sterilizing culture medium, and other equipment for culturing microalgae and treating the resulting biomass. One consequence of this phenomenon is the premature degradation of tools used for biomass production and treatment (downstream processing, or DSP).

To avoid this degradation problem, equipment made of particular alloys more resistant to chloride ions can be used. These materials with greater salt-resistance are more expensive. In this case, production investment costs are substantially higher.

Furthermore, the use of sodium chloride (or other sodium salts, for example of type sodium sulfate, sodium carbonate) results in significant extra expenditures in terms of effluent treatment, particularly water desalination.

Lastly, the presence of sodium salts in the oil cake-type coproducts constituted by the biomass remaining after oil extraction makes their valorization more difficult, particularly for animal feed, fish farming, or as an ingredient for cosmetics or in the pharmaceutical industry.

U.S. Pat. No. 5,518,918 describes the replacement of sodium chloride with other types of sodium salts (sodium sulfate, sodium carbonate, etc.). Even if that makes it possible to avoid the premature wear of stainless steel equipment, adding sodium salts to the medium does not make it possible to avoid the additional costs related to effluent treatment, nor the problems of valorization of the coproducts mentioned above.

Moreover, replacing NaCl with another sodium salt results in additional costs related to the purchase of the substitute salt.

In the article titled "Optimization of docosahexaenoic acid production by *Schizochytrium limacinum* SR21" by Yokochi et al. [(1998) *Appl. Microbiol. Vol.* 49, pp. 72-76], the tolerance of the strain *Schizochytrium limacinum* SR21 for salt conditions was studied. The strain had a wide tolerance for high salt concentrations, the concentration being between 50% and 200% of that of seawater. The growth of the strain in the culture without salt was half that in the culture containing 50% seawater. We note that the basal culture medium used in this study also contained 3% glucose and 1% yeast extract. A claimed culture medium "without salt" or having a "low concentration" of salt is described in U.S. Pat. No. 8,900,831. However, as for Yokoshi et al., the addition of yeast extract is needed for microalgal growth. However, such a medium supplemented with yeast extract contains more than 30 mg of chloride salts and sodium salts.

What is more, the addition of yeast extract represents an additional cost for the medium, and also a disadvantage in terms of the quality of the final biomass for use as a food product or a pharmaceutical product. Yeast extracts are not standardized products and thus batches of yeast extracts are not homogeneous. This has an impact, therefore, on the homogeneity of the end products derived from the biomass of a culture medium containing yeast extracts.

Shabala et al. ["Osmotic adjustment and requirement for sodium in marine protist thraustochytrid" (2009) *Environmental Microbiology* Vol. 11(7), pp. 1835-1843] showed that *Thraustochytrium* can grow in culture medium with low sodium content (1 mM), provided that the medium is supplemented with a compound such as mannitol or sucrose, which allows the osmotic adjustment of this sodium-free culture medium. However, the presence of the latter compounds results in extra expenditures associated with the cost of these materials. Moreover, in spite of the addition of compounds that adjust the osmolarity of the culture medium, the biomass yields (200,000 cells per milliliter) obtained without salt and with mannitol remain insufficient for industrial production of DHA.

In a recent article by Shabala et al. ["Thraustochytrids can be grown in low-salt media without affecting PUFA production", *Marine Biotechnology* (2013) 15: 437-444], a mutant was obtained by UV-induced random mutagenesis of *Schizochytrium limacinum* SR21—named OUC88—and tested to determine the environmental factors which induce a change in the fatty acid composition. FIG. 2 of the article shows that, when the salt concentration falls below 0.9%, the biomass and the quantity of lipids greatly decrease (less than 20 g/L in biomass and less than 10 g/L in lipids).

It is desirable to be able to culture Thraustochytrids under optimal conditions in order to increase the yield of the fatty acid(s) to be produced, while avoiding the problems related to the wear of steel equipment, while reducing the production costs for fermentation, as well as for the treatment of the resulting biomass. In particular, it is desirable to provide methods for culturing *Aurantiochytrium* which make it possible to reduce, even substantially to eliminate, sodium ions and chloride ions in the culture media, without the addition of other culture components, which can result in extra expenditures related to the treatment of effluents, as well as extra expenditures related to additional DSP steps and problems of valorization of the end products.

In the context of the present invention, it is desirable to obtain a biomass and lipid yield sufficient for an industrial production of DHA. It is thus desirable to obtain yields, for example, higher than 100 g/L of dry matter, preferably higher than 130 g/L of dry matter, more preferentially still higher than 150 g/L of dry matter. It is thus desirable to obtain, for example, more than 40%, even 50% of fatty acids in relation to the total weight of the dry matter. It is also desirable to obtain, for example, more than 30%, even 40% of DHA in the fatty acids in relation to the total weight of the dry matter.

Thus, it is at the conclusion of numerous strain screening experiments that the applicant succeeded in identifying strains of protists of the genus *Aurantiochytrium*, able to grow in a chemically defined culture medium with no addition of sodium, nor of chloride, nor of an organic source such as yeast extract, nor of osmotic agents such as mannitol, or sucrose, as defined in the articles by Shabala et al. (2013) (or other osmotic agents such as sorbitol, polyethylene glycol (PEG)).

These strains, cultured under the conditions of the present invention, make it possible to obtain a production with a high yield of biomass (higher than 110 g/L, preferably 120 g/L) and of polyunsaturated fatty acids (higher than 15 g/L, preferably 20 g/L), particularly of DHA.

One strain (FCC 1324) concerned by the invention, representative of the *Aurantiochytrium* strains thus isolated and selected, was deposited with and accepted by the CCAP (Culture Collection of Algae and Protozoa, Scottish Association for Marine Science, Dunstaffnage Marine Laboratory, Oban, Argyll PA371QA, Scotland, United Kingdom) on 21 Jun. 2013, according to the provisions of 10 the Budapest Treaty, under accession number CCAP 4062/1 by Applicant FERMENTALG, 4 Rue Riviere, Libourne 33500 France.

FIG. 1: Phylogenetic analysis showing the relationships between the DNA sequences encoding the small subunit ribosomal RNA. The sequences were aligned with ClustalW of Mega 5.1. The analysis was carried out using the maximum-likelihood method. The Thraustochytrid strains used in this study belong to the genera: *Aurantiochytrium mangrovei*, *Schizochytrium* sp., and *Schizochytrium aggregatum*, *Ulkenia visurgensis*, *Ulkenia* sp., *Ulkenia profunda*, *Botryochytrium* sp., *Botryochytrium radiatum*, *Parieticytrium* sp., *Parieticytrium sarkarianum*, *Aplanochtytrium kerguelense*, *Aplanochtytrium stocchinoi*, *Oblongichytrium multirudimentale*, *Oblongichytrium* sp. and *Phytophthora infestans*. The bootstrap values are considered significant if they are higher than 75%.

(A) and (B): A comparison of fatty acid profiles between the genus according to the invention, exemplified by *Aurantiochytrium mangrovei*, of which *Aurantiochytrium limacinum* is a member (first three lines of the panels), and the genus *Schizochytrium* sp., which includes the strains ATCC 20888, as well as the strains *Aurantiochytrium* sp. SEK 217 and SEK 209 (last three lines of the panels). The culture conditions are described in Example 2.

(A) and (B): Lipid profiles of the strains according to the invention. (A) Polyunsaturated fatty acids (PUFAs) expressed as percentages in relation to the total PUFAs. (B) Saturated acids expressed as percentages in relation to the total saturated fatty acids. The cultures, the pH of which was adjusted by KOH or $NH_4OH$, were identified by the abbreviations (KOH) or (NH$_4$OH), respectively. The culture conditions are described in Examples 3 and 4.

DETAILED DESCRIPTION

By "strain" is meant not only natural strains of the genus *Aurantiochytrium* defined according to the invention, but also mutants of said natural strains.

By "chemically defined" is meant any product or mixture of products of which the chemical composition is known and of which the content of each element which constitutes the product or the mixture is also known.

By "chemically defined culture medium" is meant culture medium in which the content of each element is known, i.e. in the absence of yeast extracts or other complex sources of proteins or other organic matter such as peptone or another complex growth agent of which the composition is variable both in nature and in the absence of a fixed concentration of each of these components.

By "osmotic regulatory agent" is meant an agent present in a culture medium which makes it possible to maintain the osmotic pressure in the medium.

By "genetic identity" is meant an identity between two DNA sequences, such as evaluated by a BLAST-type software.

The present invention thus has as an object a method for culturing certain protists of the *Aurantiochytrium mangrovei* and *Aurantiochytrium limacinum* type in heterotrophic or mixotrophic mode in an organic medium substantially free of sodium (Na$^+$) and chloride (Cl$^-$). This culture method makes it possible to obtain high yields of biomass, of lipids, and specifically of DHA.

The strains concerned by the invention have the ability to grow at high density, in chemically defined culture media, without the addition of significant amounts of chloride ions or sodium ions, and without the addition of osmotic regulatory agents, such as mannitol, sorbitol or polyethylene glycol. They are, according to recent phylogenetic classifications, Thraustochytrid strains of the *Aurantiochytrium mangrovei* and *Aurantiochytrium limacinum* type, known to produce DHA [Yokoyama R, et al. (2007). Taxonomic rearrangement of the genus *Ulkenia* sensu lato based on morphology, chemotaxonomical characteristics, and 18S rRNA gene phylogeny (Thraustochytriaceae, Labyrinthulomycetes): emendation for *Ulkenia* and erection of *Botryochytrium, Parietichytrium. Mycoscience.* 48(6) p. 329-341; Yokoyama, R., Honda, D. (2007) Taxonomic rearrangement of the genus *Schizochytrium* sensu lato based on morphology, chemotaxonomical characteristics and 18S rRNA gene phylogeny (Thraustochytriaceae, Labyrinthulomycetes, stramenopiles): emendation for *Schizochytrium* and erection of *Aurantiochytrium* and *Oblongichytrium* gen. nov. *Mycoscience* 48, 199-211; Tsui C K, et al. (2009) Labyrinthulomycetes phylogeny and its implications for the evolutionary loss of chloroplasts and gain of ectoplasmic gliding. *Mol Phylogenet Evol.* 50(1): p. 129-40].

It should be recalled that conventionally, heterotrophic cultures of these microalgae genera were carried out with a seawater-based culture medium, like that used by the American Type Culture Collection, the medium ATCC 790 By+ (1.0 g yeast extract, 1.0 g peptone, 5.0 g D(+)-glucose and 1 liter seawater).

The strains are characterized genetically, as well as by their lipid profile.

The strains concerned by the invention are characterized by the genetic identity of four of their genes, 18s, actin, tubulin and EF1-alpha, to genes of a strain representative of the strains of invention, strain FCC 1324. Strain FCC 1324 is representative of the novel *Aurantiochytrium* strains thus isolated and selected, and was deposited with the CCAP (Culture Collection of Algae and Protozoa, Scottish Association for Marine Science, Dunstaffnage Marine Laboratory, Oban, Argyll PA371QA, Scotland, United Kingdom) on 21 Jun. 2013, according to the provisions of the Budapest Treaty, under accession number CCAP 4062/1.

Table 1(a) is a comparison of the sequences of four genes between the genus *Aurantiochytrium mangrovei* and the genetically closest genus *Schizochytrium* sp., as well as other genetically close strains. All the strains with sequences having between 91% and 100% identity with the genes of strain CCAP 4062-1, according to the genes compared, can be regarded as being genus *Aurantiochytrium*. A genetic identity of at least 92% to the CCAP 4062-1 18s gene concerned characterizes the strains according to the invention.

TABLE 1(a)

| 18s | | |
|---|---|---|
| *Schizochytrium* sp. strains | Length of the compared sequences (%) | % identity with CCAP 4062-1 |
| *Aurantiochytrium*_sp_SEK209_AB290574 | 99% | 91% |
| *Thraustochytriidae*_sp_MBIC11093_AB183664 | 100% | 91% |
| *Aurantiochytrium*_sp_AB073308 | 94% | 91% |
| *Aurantiochytrium*_sp_ATCC_PRA276_DQ836628 | 93% | 91% |
| *Schizochytrium*_sp_ATCC20888_DQ367050 | 100% | 91% |
| *Thraustochytriidae*_sp_BURABG162_DQ100295 | 100% | 91% |
| *Aurantiochytrium*_sp_AB052555 | 100% | 91% |
| *Aurantiochytrium*_sp_SEK217_AB290572 | 100% | 91% |
| *Aurantiochytrium*_sp_SEK_218_AB290573 | 99% | 90% |
| *Aurantiochytrium mangrovei* strains | Length of the compared sequences (%) | % identity with CCAP 4062-1 |
| *Aurantiochytrium_limacinum*_AB022107 | 77% | 96% |
| *Aurantiochytrium_limacinum*_HM042909 | 100% | 98% |
| *Aurantiochytrium_limacinum*_SL1101_JN986842 | 100% | 98% |
| *Aurantiochytrium_mangrovei*_DQ367049 | 100% | 99% |
| *Aurantiochytrium*_sp_BL10_FJ821477 | 100% | 98% |
| *Aurantiochytrium*_sp_LY2012_JX847370 | 100% | 98% |
| *Schizochytrium_limacinum*_OUC166_HM042907 | 100% | 99% |

TABLE 1(a)-continued

| | | |
|---|---|---|
| Thraustochytriidae_sp_NIOS1_AY705769 | 100% | 99% |
| Thraustochytriidae_sp_LY2012_JX847378 | 83% | 98% |
| Schizochytrium_sp_KGS2_KC297137 | 77% | 98% |
| Aurantiochytrium_sp_LY_2012_PKU_Mn5_JX847361 | 100% | 98% |
| Aurantiochytrium_limacinum_JN986842 | 100% | 98% |
| Schizochytrium_sp_SKA10_JQ248009 | 99% | 98% |
| Aurantiochytrium_sp_SD116 | 100% | 99% |

Actin

| Strains | Length of the compared sequences (%) | % identity with CCAP 4062-1 |
|---|---|---|
| Aurantiochytrium mangrovei DQ356659 | 97% | 99% |
| Schizochytrium sp. ATCC 20888 DQ356660 | 98% | 95% |
| Thraustochytrium aureum DQ356666 | 98% | 90% |
| Japonochytrium marinum DQ356668 | 96% | 89% |
| Thraustochytriidae sp. #32 DQ356663 | 96% | 89% |
| Thraustochytrium aggregatum DQ356662 | 96% | 89% |
| Schizochytrium aggregatum DQ356661 | 86% | 92% |
| Thraustochytrium striatum DQ356665 | 95% | 88% |
| Thraustochytriidae sp. RT49 DQ356669 | 91% | 89% |

EF1

| Strains | Length of the compared sequences (%) | % identity with CCAP 4062-1 |
|---|---|---|
| Aurantiochytrium mangrovei | 100% | 99% |
| Schizochytrium sp. ATCC 20888 | 100% | 94% |
| Schizochytrium aggregatum | 100% | 87% |
| Thraustochytrium striatum | 99% | 86% |
| Thraustochytriidae sp. Thel2 | 91% | 87% |
| Thraustochytriidae sp. RT49 | 100% | 84% |

Tubulin

| Strains | Length of the compared sequences (%) | % identity with CCAP 4062-1 |
|---|---|---|
| Aurantiochytrium mangrovei DQ323157 | 100% | 97% |
| Schizochytrium sp. ATCC 20111 DQ323158* | 100% | 90% |
| Schizochytrium aggregatum DQ323159 | 100% | 87% |
| Japonochytrium marinum DQ323166 | 99% | 87% |
| Thraustochytriidae sp. RT49 DQ323167 | 99% | 87% |
| Thraustochytrium kinnei DQ323165 | 99% | 87% |
| Thraustochytrium striatum DQ323163 | 99% | 86% |
| Thraustochytriidae sp. Thel2 DQ323162 | 99% | 86% |
| Thraustochytriidae sp. #32 DQ323161 | 99% | 85% |

*Schizochytrium sp. ATCC 20111 DC2323158 = ATCC 20888

The strains having a genetic identity of at least 92% for the 18s genes (SEQ NO. 1) are concerned by the invention and are thus likely to grow in a low-sodium and low-chloride medium. The applicants also noted that these strains thus defined by their genetic identity for the 18s gene have a genetic identity of at least 96% for the actin gene (SEQ NO. 2), at least 91% for the tubulin gene (SEQ NO. 3) and at least 95% for the EF1-alpha gene (SEQ NO. 4). These percentages identity are presented in Table 1 (b).

TABLE 1(b)

| | 18s | Actin | Tubulin | EF1-a |
|---|---|---|---|---|
| Percentage genetic identity: The strains of the invention have an identity with the genes of strain CCAP 4062-1 of at least: | 92% | 96% | 91% | 95% |

Figure 1:
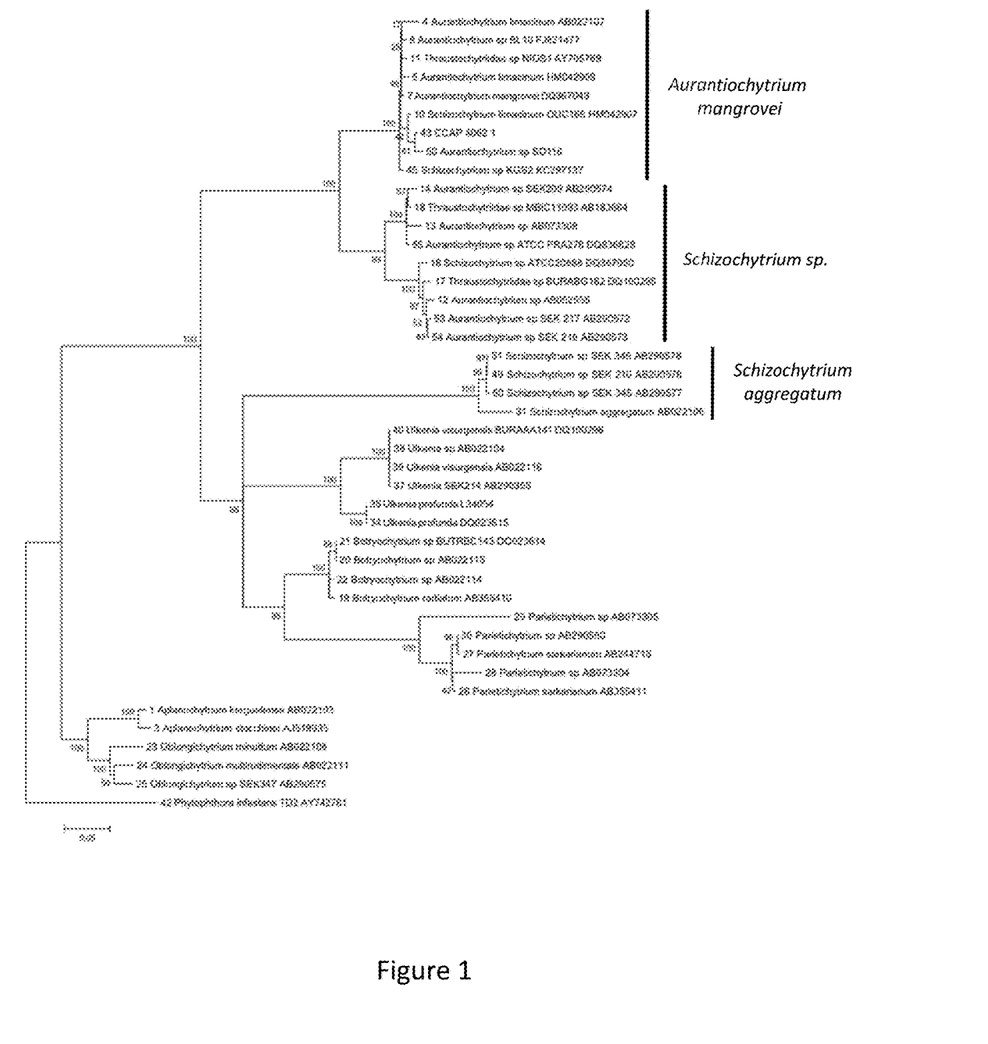

FIG. 1 shows the phylogenetic analysis which led to this definition of the strains concerned by the invention.

The Thraustochytrid strains used in this study are members of the genus Aurantiochytrium mangrovei, Schizochytrium sp. and Schizochytrium aggregatum.

The sequences were aligned with CLUSTAL W of Mega 5.1. In the Figure, the numbers located at the branches are bootstrap values.

A bootstrap value of 70% is regarded as the lower limit for the branch between two groups to be significant. According to Hillis D. M. and Bull J. J. in their article "An empirical test of bootstrapping as a method for assessing confidence in phylogenetic analysis" [(1993) Systematic Biology Vol. 42, pp. 182-192], bootstrap proportions of more than 70% usually correspond to a probability of at least 95% that the corresponding clade (groups) is real.

In FIG. 1, this means that the difference between the A. mangrovei and Schizochytrium sp. groups is significant because the node separating the two groups has a value of 100%, and thus that two different genera are present. These two groups are themselves very distant from the Schizochytrium aggregatum group, as had already been shown by Yokoyama and Honda [(2007), Taxonomic rearrangement of the genus Schizochytrium sensu lato based on morphology, chemotaxonomic characteristics, and 18S rRNA gene phylogeny (Thraustochytriaceae, Labyrinthulomycetes): emendation for *Schizochytrium* and erection of *Aurantiochytrium* and *Oblongichytrium* gen. nov.; *Mycoscience* Vol. 48, pp. 99-211].

In FIG. 1, the strains concerned by the invention are those of the first group at the top of the Figure and have the name *Aurantiochytrium mangrovei*.

As examples of the strains concerned by the invention, mention may be made of the strains *Aurantiochytrium* sp. SD116 (JX863672), *Aurantiochytrium limacinum* (AB022107), *Aurantiochytrium mangrovei* (DQ367049), *Aurantiochytrium limacinum* SL1101 (JN986842), *Aurantiochytrium limacinum* (JN986842), *Aurantiochytrium* sp. LY2012 (JX847370), *Aurantiochytrium limacinum* (HM042909) and *Aurantiochytrium* sp. BL10 (FJ821477), in the phylogenetic class classified as identified by the inventors. The numbers in parentheses are accession numbers.

Indeed, each of these strains has a percentage identity to the sequences of strain CCAP 4062/1 of at least 92%, 96%, 91% and 94% to sequences SEQ NO. 1, SEQ NO. 2, SEQ NO. 3 and SEQ NO. 4, respectively.

For example, strains of the genus *Aurantiochytrium* having a genetic identity of 92%, 93%, 94%, 95%, 96%, 97%, 98%, 99% or 100% to sequence SEQ NO. 1 are concerned by the invention. These strains also have a genetic identity of 96%, 97%, 98%, 99% or 100% to sequence SEQ NO. 2, a genetic identity of 91%, 92%, 93%, 94%, 95%, 96%, 97%, 98%, 99% or 100% to sequence SEQ NO. 3 and a genetic identity of 95%, 96%, 97%, 98%, 99% or 100% to sequence SEQ NO. 4.

Table 1(a) shows in detail the comparison of the genetic identities of the strains concerned, or not, by the invention, with strain CCAP 4062/1.

It is noted that neither the strain *Schizochytrium* sp. ATCC 20888 (DQ367050) nor the strain FCC1412 *Schizochytrium* sp. SEK 209 (AB290574) is a member of the strains concerned by the invention. The identity values to SEQ NO. 1 for these strains are 91%.

These strains have the ability to grow at high density in a chemically defined culture medium (i.e. in the absence of yeast extract or other protein extracts) having very small amounts of sodium chloride. This medium is characterized by the fact that it contains less than 3.5 g/L, preferably less than 1 g/L, more preferentially less than 10 mg/L of sodium ions and less than 1 g/L, preferably less than 0.5 g/L, more preferentially less than 0.2 g/L of chloride ions.

Figure 2:
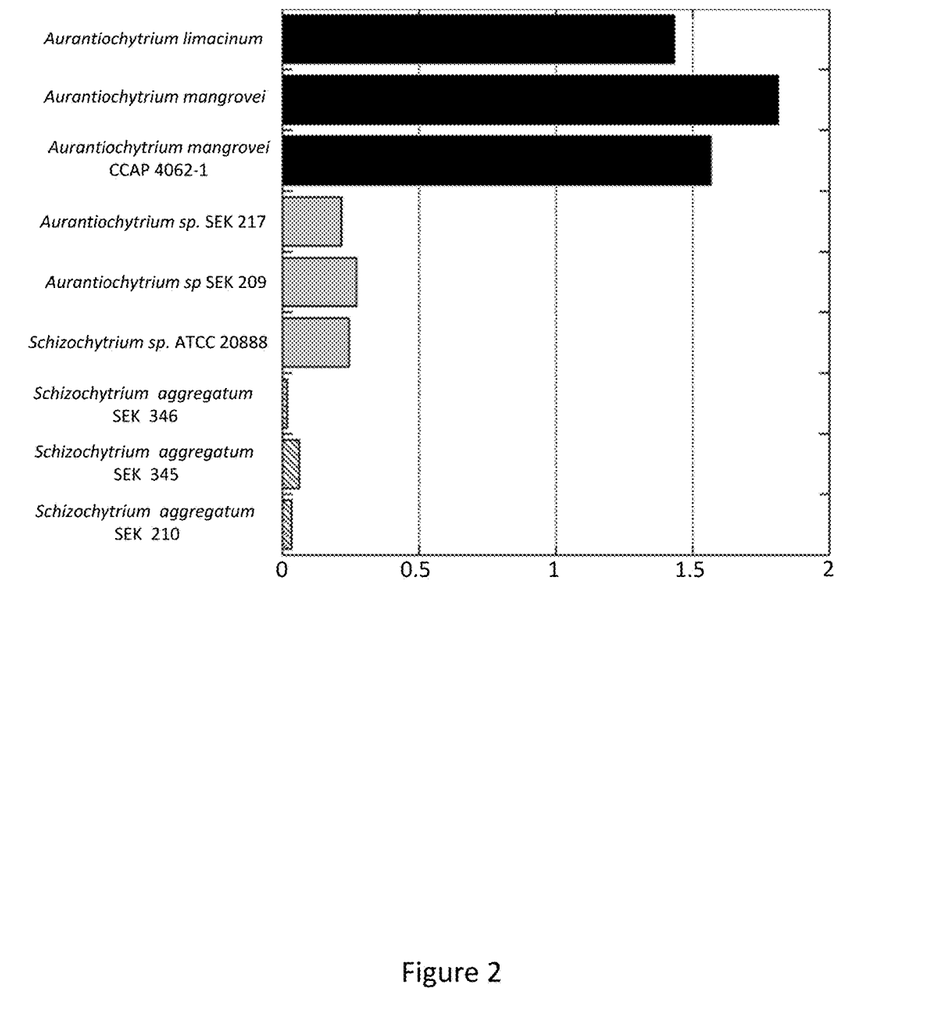
FIG. 2: Tests of growth in Erlenmeyer flasks with FCC-M medium having a low $Na^+$ and $Cl^-$ content. Comparison of the growth of the strains concerned by the invention (in black) and not concerned by the invention (in gray and with lines) in a culture medium according to an embodiment of the invention. The length of the column for each strain represents optical density (Example 1).

In Example 1, the applicants carried out growth tests in Erlenmeyer flasks with the strains according to the invention, as well as comparative strains not concerned by the invention, in such a culture medium (see Table 2(a) for the principal culture medium). The cultures were prepared in the presence of inorganic nitrogen $(NH_4)_2SO_4$, and glucose as carbon source, and with no organic nitrogen supply. Thus, FIG. 2 illustrates the results of these experiments. The results show that all the *Aurantiochytrium mangrovei* strains have the ability to grow on this medium, unlike the other Thraustochytrid genera tested, *Schizochytrium* sp. and *Schizochytrium aggregatum*.

It is noted that the strains according to the invention have a genetic identity for the 18s, actin, tubulin and EF1-alpha genes of at least 92%, 96%, 91% and 95%, respectively, of strain FCC 1324.

The strains concerned by the invention are also characterized by their lipid profile. Strain CCAP 4062/1 is taken as example and representative of the strains according to the invention.

Figure 3:
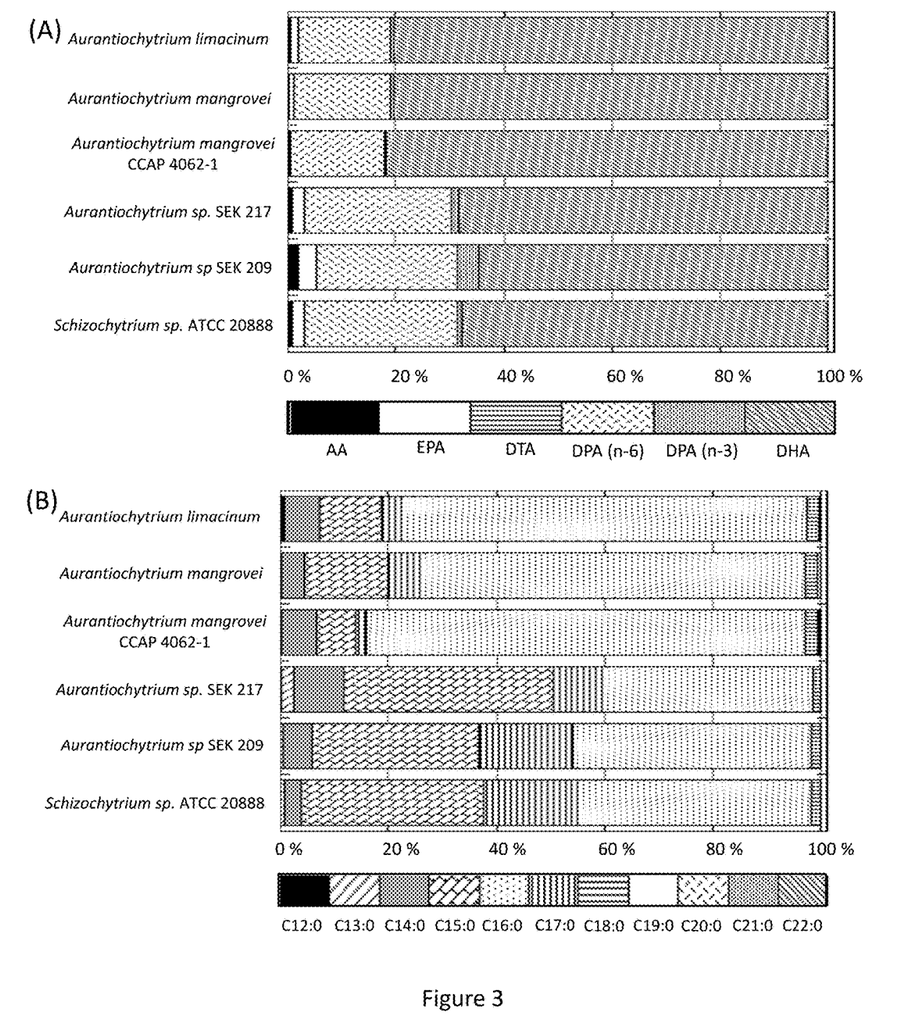
FIG. 3: Fatty acid profiles of the various Thraustochytrid strains cultured in Erlenmeyer flasks (Example 2).

FIGS. 3(A) and 3(B) show a comparison of the fatty acid profiles between the strains of two different genera. The genus according to invention, illustrated by *Aurantiochytrium mangrovei*, of which *Aurantiochytrium limacinum* is part (first three lines of each panel) and the genus *Schizochytrium* sp., which includes the strains ATCC 20888, as well as the strains *Aurantiochytrium* sp. SEK 217 and SEK 209 (last three lines of each panel). The lipid profile of the genus *Aurantiochytrium mangrovei* has a majority of DHA (higher than 80% of the total PUFAs) in the culture conditions according to an embodiment of the invention, described in Example 2.

In FIG. 3(A), it is seen that the strains ATCC 20888, *Aurantiochytrium* sp. SEK 217 and SEK 209 have a different profile with more EPA in relation to the strains according to the invention.

DPA (n-6) represents about 20% of the total PUFAs with minor amounts of AA and EPA (see FIG. 3(A)). Other strains which have a genetic similarity to strain CCAP 4062/1 also exhibit this profile.

FIG. 3(B) shows that the strains ATCC 20888, *Aurantiochytrium* sp. SEK 217 and SEK 209 have a different saturated fatty acid profile, with less palmitic acid and a greater amount of odd fatty acid C15:0 and C17:0.

Figure 4:
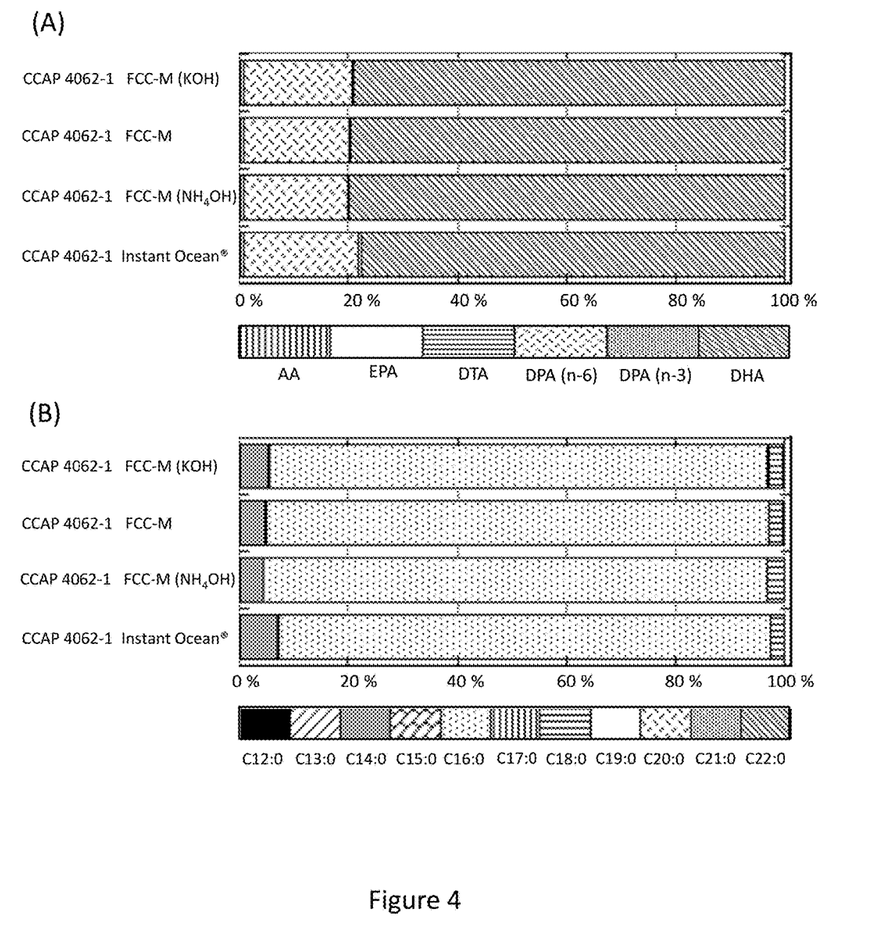
FIG. 4: Fatty acid profiles of the various Thraustochytrid strains cultured in a bioreactor (Examples 3 and 4).

FIG. 4(A) shows the polyunsaturated fatty acids (PUFAs) expressed in percentages in relation to the total PUFAs. FIG. 4(B) shows the saturated fatty acids expressed in percentages in relation to the total saturated fatty acids. The cultures whose pH was adjusted with KOH or $NH_4OH$ were identified by the abbreviations (KOH) or ($NH_4OH$), respectively. The profile remains virtually unchanged according to the culture conditions. DHA is the majority polyunsaturated fatty acid, at almost 80% of the total unsaturated acids. C16:0 remains the majority saturated fatty acid, at more than 90% of the total saturated acids, in the culture conditions according to an embodiment of the invention, described in Examples 3 and 4.

Thus, the inventors defined the strains concerned by the invention. These strains have an ability to grow at high density in chemically defined culture medium, without the addition of significant amounts of sodium or chloride.

The culture of these strains is generally carried out in heterotrophic mode.

The chemically defined culture medium according to the invention contains a carbon source, a nitrogen source and salts necessary to microorganism growth. The person skilled in the art knows well the elements necessary to microorganism growth in a fermentation process.

According to a preferred embodiment of the invention, the carbon source is a chemically defined source selected from glucose and glycerol, preferably glucose.

The carbon source content in the culture medium is advantageously between 10 and 90 g/L, or 10 and 75 g/L.

The nitrogen source is advantageously a chemically defined inorganic or organic source, with the exception of any complex organic matter containing nitrogen, such as yeast extracts or mixtures of protein extracts.

Preferentially, the nitrogen source is an ammonium salt, particularly ammonium sulfate, and/or a nitrate, particularly potassium nitrate.

The nitrogen source content in the culture medium is advantageously between 1 and 10 g/L.

The principal culture medium may contain all the other components known to the person skilled in the art for culturing microalgae according to the invention. The medium generally contains chemically defined inorganic salts, for example alkaline and alkaline-earth metal salts, as well as salts of other metals. For example, mention may be made of Ca, Mg, K, Fe, Ni, Co, Cu, Mn, Mo or Zn salts. For example, mention may be made of sulfates such as potassium sulfate, magnesium sulfate, iron sulfate, ammonium sulfate, magnesium sulfate, or copper sulfate, nickel sulfate, zinc sulfate. Mention also may be made of phosphates such as potassium acid phosphate, or carbonates such as calcium carbonate. Mention may also be made of chlorides such as cobalt chloride, manganese chloride, calcium chloride. Mention may also be made of alkali metal oxides. Mention may also be made of selenites and molybdates such as sodium molybdate and sodium selenite. Other usable inorganic salts are, for example, halides, such as potassium bromide or potassium iodide.

The contents of the various salts in the culture medium depend on the microorganisms' needs in terms of growth. Certain salts are employed only in small amounts as a supply of trace elements, such as zinc, cobalt, manganese, molybdenum, selenium, nickel or copper salts.

A particularly preferred culture medium for the method of the invention contains, if need be, aside from other elements such as, for example, nutrient components, at least one salt selected from the group consisting of magnesium sulfate, calcium chloride, potassium borate and phosphate. The salt(s) is/are added without the total salt content according to the invention being exceeded. It is particularly preferred when magnesium sulfate, calcium chloride and potassium phosphate are added to the medium.

Advantageously, the ion content is comprised in the ranges detailed in Table 2(a) (see following table).

In all cases, the nature and the proportions of these salts in the culture medium are selected so that the sodium ion content is less than 3.5 g/L, preferably less than 1 g/L, more preferentially less than 10 mg/L, and that the chloride ion content is less than 1 g/L, preferably less than 500 mg/L, more preferentially about 200 mg/L.

According to a preferential embodiment of the invention, the culture medium also contains additional macro- or micronutrients, such as amino acids, purine, pyrimidine, chemically defined vitamins, i.e. other than the macro- or micronutrients supplied in the culture medium by complex sources, such as yeast. Generally, the medium contains other media components known to the person skilled in the art. Anti-foaming agents may be added, if need be. However, the medium does not contain complex components that cannot be chemically defined.

The vitamins are advantageously selected from thiamin, vitamin B12, pantothenate and mixtures thereof.

The vitamin content in the culture medium is advantageously between the values described in Table 2(a).

According to a preferential embodiment of the invention, the chemically defined culture medium consists of a mixture of a chemically defined carbon source, a chemically defined nitrogen source, salts and chemically defined vitamins.

It will be noted that this culture medium is particularly suitable for a culture in a fermentor, advantageously in fermentors of at least 1000 liters, particularly in so-called "batch" discontinuous mode, in so-called "fed batch" semi-continuous mode, or in continuous mode.

An example of a culture medium according to an embodiment of the invention is defined as in Table 2(b) below.

TABLE 2(a)

General composition of the medium.

| | | Concentration ranges | | |
|---|---|---|---|---|
| Ingredients | Concentration | General | Preferred | More preferred |
| Principal Solution | | | | |
| KCl | g/L | 0-1 | 0.05-5 | 0.1-0.5 |
| $H_3BO_3$ | g/L | 0-0.5 | 0.01-0.3 | 0.1-0.2 |
| $MgSO_4, 7H_2O$ | g/L | 0.5-13 | 2-10 | 5-7 |
| $CaCl_2, 2H_2O$ | g/L | 0.1-1.1 | 0.2-0.9 | 0.3-0.6 |
| $KNO_3$ | g/L | 0-0.1 | 0.01-0.06 | 0.02-0.05 |
| $KH_2PO_4, 7H2O$ | g/L | 0.1-1.5 | 0.2-1 | 0.3-0.7 |
| $Na_2EDTA, 2H_2O$ | g/L | 0-0.01 | 0.001-0.005 | 0.002-0.004 |
| $ZnSO_4 \cdot 7H_2O$ | mg/L | 0.001-0.1 | 0.01-0.1 | 0.02-0.08 |
| $CoCl_2 \cdot 6H_2O$ | mg/L | 0.001-0.1 | 0.01-0.1 | 0.02-0.08 |
| $MnCl_2 \cdot 4H_2O$ | mg/L | 0.01-2 | 0.05-1 | 0.25-0.7 |
| $Na_2MoO_4, 2H_2O$ | mg/L | 0.0001-1 | 0.0005-0.1 | 0.001-0.1 |
| $Na_2SeO_3$ | mg/L | 0-1 | 0.01-0.5. | 0.01-0.02 |
| $NiSO_4 \cdot 6H_2O$ | mg/L | 0.0001-50 | 0.5-5 | 0.001-0.006 |
| $CuSO_4 \cdot 5H_2O$ | mg/L | 0.001-3 | 0.0025-1 | 0.005-0.02 |
| EDTA—Fe | mg/L | 1-100 | 10-50 | 20-40 |
| Carbon | | | | |
| Glucose | g/L | 10-90 | 20-60 | 45-60 |
| Nitrogen | | | | |
| $(NH_4)_2SO_4$ | g/L | 1-10 | 2-9 | 6-8 |
| Post Autoclave Vitamins | | | | |
| Thiamine | mg/L | 0.1-100 | 1-50 | 5-10 |
| Vitamin B12 | mg/L | 0.01-100 | 0.025-5 | 0.1-2 |
| Pantothenate | mg/L | 0.1-100 | 0.1-25 | 1-10 |

TABLE 2(b)

Example culture medium.

| Principal Solution | | |
|---|---|---|
| KCl | 0.30 | g/L |
| $H_3BO_3$ | 0.0175 | g/L |
| $MgSO_4, 7H_2O$ | 5.25 | g/L |
| $CaCl_2, 2H_2O$ | 0.45 | g/L |
| $KNO_3$ | 0.04 | g/L |
| $KH_2PO_4, 7H_2O$ | 0.309 | g/L |
| $Na_2EDTA, 2H_2O$ | 0.0020 | g/L |
| $ZnSO_4 \cdot 7H_2O$ | 0.08 | mg/L |
| $CoCl_2 \cdot 6H_2O$ | 0.08 | mg/L |
| $MnCl_2 \cdot 4H_2O$ | 0.40 | mg/L |
| $Na_2MoO_4, 2H_2O$ | 0.00100 | mg/L |
| $Na_2SeO_3$ | 0.00173 | mg/L |
| $NiSO_4 \cdot 6H_2O$ | 0.00500 | mg/L |
| $CuSO_4 \cdot 5H_2O$ | 0.015 | mg/L |
| EDTA—Fe | 20 | mg/L |
| Carbon | | |
| Glucose | 50 | g/L |
| Nitrogen | | |
| $(NH_4)_2SO_4$ | 8 | g/L |
| Post Autoclave Vitamins | | |
| Thiamine | 6 | mg/L |
| Vitamin B12 | 0.15 | mg/L |
| Pantothenate | 4.0 | mg/L |

An example of a culture medium according to an embodiment of the invention is defined as in Table 2(c) below. This medium, named FCC-M, contains 0.00038 g/L of sodium ($Na^+$) and 0.437 g/L of chloride ($Cl^-$). The medium does not contain added NaCl.

TABLE 2(c)

FCC-M culture medium.

| Ingredients | Concentration g/L |
|---|---|
| Principal Solution | |
| KCl | 0.36 |
| $H_3BO_3$ | 0.175 |
| $MgSO_4, 7H_2O$ | 6.750 |
| $CaCl_2, 2H_2O$ | 0.55 |
| $KNO_3$ | 0.04667 |
| $KH_2PO_4, 7H_2O$ | 0.30940 |
| $Na_2EDTA, 2H_2O$ | 0.003094 |
| $ZnSO_4 \cdot 7H_2O$ | 0.000073 |
| $CoCl_2 \cdot 6H_2O$ | 0.000016 |
| $MnCl_2 \cdot 4H_2O$ | 0.00054 |
| $Na_2MoO_4, 2H_2O$ | 0.00000148 |
| $Na_2SeO_3$ | 0.00000173 |
| $NiSO_4 \cdot 6H_2O$ | 0.00000298 |
| $CuSO_4 \cdot 5H_2O$ | 0.0000098 |
| EDTA—Fe | 0.03 |
| Carbon | |
| Glucose | 55 |
| Nitrogen | |
| $(NH_4)_2SO_4$ | 7 |
| Post Autoclave | |
| Vitamins | |
| Thiamine | 0.008 |
| Vitamin B12 | 0.00013 |
| Pantothenate | 0.0027 |

Conventionally, during the culture of the strains according to the invention in a bioreactor or a fermentor, in heterotrophic or mixotrophic conditions, the basal culture medium is supplemented with an addition solution in order to maintain microalgal growth. The carbon-containing substrate, for example glucose, may also be added (addition solution 2). The person skilled in the art knows how to determine the concentration of each element of the addition solution. For example, the contents of the elements by way of example are indicated in Table 3(a) below.

TABLE 3(a)

Example of addition solutions 1 and 2 for a culture in a fermentor or a bioreactor.

| | g/L |
|---|---|
| Addition solution 1 | |
| $K_2SO_4$ | 0-35 |
| $MgSO_4, 7H_2O$ | 0-30 |
| $KH_2PO_4, 7H_2O$ | 50-70 |
| $FeSO_4, 7H_2O$ | 0-1 |
| $(NH_4)_2SO_4$* | 120-150 |
| $MnCl_2$ $4H_2O$ | 0.10-0.2 |
| $ZnSO_4 \cdot 7H_2O$ | 0.1-0.2 |
| $CoCl_2 \cdot 6H_2O$ | 0.001-0.002 |
| $Na_2MoO_4, 2H_2O$ | 0.001-0.002 |
| $CuSO_4, 5H_2O$ | 0.05-0.2 |
| $NiSO_4, 6H_2O$ | 0.05-0.2 |
| $Na_2EDTA, 2H_2O$ | 1-3 |
| Thiamine | 1-2 |
| Vitamin B12 | 0.005-0.02 |
| Pantothenate | 0.05-0.3 |
| Addition solution 2 | |
| Glucose | 150-850 |
| $KH_2PO_4$ | 4-7 |
| $(NH_4)_2SO_4$* | 20-40 |

An example of such addition solutions is given in Table 3(b).

TABLE 3(b)

Example of addition solutions 1 and 2 for a culture in a fermentor or a bioreactor.

| | Concentration g/L |
|---|---|
| Addition solution 1 | |
| $K_2SO_4$ | 31.9 |
| $MgSO_4, 7H_2O$ | 25.8 |
| $KH_2PO_4, 7H_2O$ | 61.38 |
| $FeSO_4, 7H_2O$ | 0.61 |
| $(NH_4)_2SO_4$* | 138.24 |
| $MnCl_2$ $4H_2O$ | 0.165 |
| $ZnSO_4 \cdot 7H_2O$ | 0.165 |
| $CoCl_2 \cdot 6H_2O$ | 0.0016 |
| $Na_2MoO_4, 2H_2O$ | 0.0016 |
| $CuSO_4, 5H_2O$ | 0.11 |
| $NiSO_4, 6H_2O$ | 0.086 |
| $Na_2EDTA, 2H_2O$ | 1.81 |
| Thiamine | 0.49 |
| Vitamin B12 | 0.008 |
| Pantothenate | 0.1656 |
| Addition solution 2 | |
| Glucose | 750 |
| $KH_2PO_4$ | 6.4 |
| $(NH_4)_2SO_4$* | 34 |

According to an embodiment of the invention, when the culture is carried out in a fermentor or a bioreactor, typically, after adding the addition solutions in order to maintain cell growth, the final $Na^+$ concentration is about 10 mg/L, preferably less than 6 mg/L, and the final $Cl^-$ concentration is about 250 mg/L, preferably less than 200 mg/L.

According to another embodiment of the invention, when the culture is carried out in Erlenmeyer flasks, the $Na^+$ concentration is less than 5 mg/L, preferably less than 2 mg/L, and more preferentially less than 1 mg/L, and the $Cl^-$ concentration is about 1 g/L, preferably less than 0.750 g/L, and more preferentially less than 0.5 g/L.

Generally, in the course of the culture, additions of an organic carbon-containing substrate are carried out (see, for example, addition solution 2 in Table 3(a or b)), in order to allow the cells to accumulate a high concentration of lipids. Additional substrate (addition solution 2) is added to the culture medium during the culture process in order to maintain a sufficient concentration. This organic carbon-containing substrate preferentially contains, in pure form or in a mixture: glucose, cellulose derivatives, sucrose and/or glycerol. The organic substrate concentration is generally between 200 mM and 500 mM.

The organic carbon-containing substrate contained in the culture medium may consist of complex molecules or a mixture of substrates. The products derived from the biotransformation of starch, for example from corn, wheat or potato, particularly starch hydrolysates, which consist of small molecules, constitute, for example, organic carbon-containing substrates suited to the heterotrophic or mixotrophic culture of the protists according to the invention.

During the culture, the pH is between 4 and 8, the temperature between 20 and 30° C. and the dissolved oxygen concentration is typically adjusted between 5% and 30%.

This method has the advantage of increasing the biomass yield obtained from the culture. It also has the advantage of enriching the protists thus cultured in polyunsaturated fatty acids, more particularly in docosahexaenoic acid (DHA).

According to an embodiment of the invention, a preculture is prepared in a culture medium having a small amount of NaCl, such as the medium FCC-M (Table 2(c)) containing, for example, yeast extract as nitrogen source, and glucose, for example, as carbon source. After an incubation period, for example 48 hours, the cells are centrifuged and the cell pellet is rinsed in culture medium having a small amount of NaCl, such as FCC-M, for example, containing neither yeast extract nor any other inorganic or organic nitrogen source. The purpose of this operation is to avoid any Na$^+$ supply in the principal culture via the presence of yeast extract in the preculture, generally corresponding to 1/100 (v/v) of the culture volume of the principal solution.

The isolated *Aurantiochytrium* strains according to the invention make it possible to produce significant amounts of biomass as well as lipids, the lipids being DHA-rich. Indeed, the method of the invention in heterotrophic or mixotrophic conditions makes it possible to obtain a biomass yield higher than 100 g/L, preferably higher than 120 g/L, this biomass having 50% to 60% of lipids in relation to the weight of the dry matter. DHA may represent more than 15%, or more than 20%, or more than 30% of the total fatty acids contained in the protists. The protists, according to an embodiment of the invention, may thus have a DHA productivity (amount of product of interest produced, per liter of culture, per hour) of at least 0.1 g/L/h, preferably at least 0.2 g/L/h, and more preferentially at least 0.3 g/L/h.

The method according to the invention further comprises the following steps:

a) culturing, in heterotrophic conditions, one or more Labyrinthulomycetes strains, particularly of the genus *Aurantiochytrium*, having a genetic identity of at least 92% to sequence SEQ NO. 1 in a chemically defined culture medium having less than 1 g/L, preferably less than 10 mg/L of sodium (Na$^+$) and less than 1 g/L, preferably less than 200 mg/L of chloride (Cl$^-$), b) a step of maintaining said culture for several generations, c) a step of recovering the biomass thus cultured.

By "step of recovering" is more particularly meant isolating the strain(s) whose number of cells increased the most over the course of said generations.

The method may also comprise additional steps:

d) a step of recovering the lipids of the strains, and optionally, e) extracting DHA (docosahexaenoic acid) from the recovered lipids.

The strains of step (a) may also have a genetic identity of at least 96% to sequence SEQ NO. 2, and/or a genetic identity of at least 91% to sequence SEQ NO. 3 and/or a genetic identity of at least 95% to sequence SEQ NO. 4.

The culture method according to the invention makes it possible to prepare cultures of these *Aurantiochytrium* strains in culture media with a low level of sodium and of chloride, without losing the productivity and the high yields of biomass, lipids and particularly DHA. Thus is avoided the degradation of fermentors and other stainless steel equipment used to culture cells and to treat the resulting biomass, as well as the premature degradation by corrosion of tools used for biomass production and treatment (downstream processing, or DSP).

The invention also relates to the development of a culture medium allowing the high cell-density production of DHA-rich strains according to the invention. The medium is chemically defined with a low content of sodium ions (Na$^+$) and chloride ions (Cl$^-$). The Na$^+$ concentration is generally less than 100 mg/L, preferably less than 50 mg/L, and more preferentially less than 6 mg/L, and the Cl$^-$ concentration is preferably less than 0.5 g/L, and more preferentially less than 200 mg/L. According to an embodiment of the invention, the culture of the strains concerned by the invention is carried out in a culture medium having less than 0.5 g/L NaCl, less than 6 mg/L of sodium ions and less than 200 mg/L of chloride ions.

According to an embodiment, the culture medium is FCC-M (Table 2(c)). If the culture is carried out in a fermentor or a bioreactor, addition solutions will be desirable, as described above (see for example Table 3(a or b)).

Since the culture media according to the invention are chemically defined, they contain neither growth agents, such as yeast extracts or peptones which, themselves as well, comprise amounts of sodium chloride, nor osmotic regulatory agents, such as mannitol or sorbitol. Thus, in the absence of these agents, the biomass and the lipids derived from the culture can be used for food products (or pharmaceutical products) without the numerous DSP steps needed either to characterize the content of the end products or to eliminate these unwanted added agents in the end products. Thus the extra costs associated with these additional steps are avoided. Likewise, the coproducts obtained after oil extraction may be used for animal feed in the form of oil cakes, for example.

Another advantage of the method of the invention and of the medium of the invention is that effluents resulting from the cultures do not contain agents requiring additional treatment steps which lead to additional costs and which thus make the production less profitable.

The method and the medium of the invention not only make it possible to optimize the production of the biomass obtained from the culture, while avoiding the use of chloride ions and sodium ions and the associated problems of extra cost, but also to enrich the organisms thus cultured in polyunsaturated fatty acids.

Preferably, the strains are cultured according to the methods described above, then recovered in order to extract the lipid content therefrom, particularly lipids including DHA. Methods of selective extraction of lipids, including DHA, are known to the person skilled in the art and are, for example, described by Bligh, E. G. and Dyer, W. J. (1959) [A rapid method of total lipid extraction and purification, *Can. J. Biochem. Physiol.*, 37:911-917].

The strains according to an embodiment of the invention thus may have a DHA productivity of at least 0.1 g/L/h, preferably at least 0.2 g/L/h, and more preferentially at least 0.3 g/L/h.

The invention also relates to the use of all or part of the biomass and/or the coproducts obtained from the method of the invention as a product, ingredient in a product for human consumption or as raw material for animal feed, particularly aquaculture.

The invention also relates to the use of the culture medium according to the embodiments described in this text, particularly the culture medium named FCC-M, for culturing protists for the production of lipids and pigments.

Example 1

Growth Tests in Erlenmeyer Flasks

The strains listed in FIG. 2 were first cultured in medium containing reconstituted sea salt (Instant Ocean®, 15 g/L) for two days, then centrifuged and washed once with FCC-M solution (Table 2(c)), before being inoculated (1/1000 v/v) in Erlenmeyer flasks containing 50 mL of FCC-M medium. The optical densities of the cell cultures were measured after three days of incubation at 26° C. with stirring (220 rpm).

Example 2

Fatty Acid Profiles of the Cells Having Grown in the Erlenmeyer Flasks

The strains listed in FIG. 2 were first cultured in medium containing reconstituted sea salt (Instant Ocean®, 15 g/L) for two days, then centrifuged and washed once with FCC-M solution (Table 2(c)), before being inoculated (1/1000 v/v) in Erlenmeyer flasks containing 50 mL of FCC-M medium, in which ammonium sulfate was substituted with yeast extract (4 g/L). The fatty acid (FAME) profile was determined from cell cultures incubated for three days at 26° C. with stirring (220 rpm).

Example 3

Tests of Growth and DHA Production in a Bioreactor

The *Aurantiochytrium* cultures were prepared in 1 to 2 L usable fermentors (bioreactors) with dedicated automatic equipment with computerized supervision. The pH of the system was adjusted by adding base (NaOH or KOH) and/or acid (sulfuric acid solution). The culture temperature was set to 26° C. Stirring was carried out by means of three stirring rotors placed on the shaft according to the Rushton configuration (three-blade impellers with down-pumping). The dissolved oxygen pressure was adjusted in the medium throughout the culture by means of stirring speed (250-1200 rpm), air flow rate (0.25-1 vvm) and oxygen flow rate (0.1-0.5 vvm). The adjustment parameters, integrated in the automated supervision system, made it possible to maintain a constant $pO_2$ between 5% and 30%. The culture time was between 50 and 200 hours, preferably between 65 and 96 hours, for example 72 hours.

A preculture was prepared on a shaking table (140 rpm) in a temperature-controlled enclosure (26° C.), in FCC-M medium, containing 4 g of yeast extract as nitrogen source and 30 g of glucose as carbon source. After 48 hours of incubation, the cells were centrifuged for 5 minutes at 3000 g and the cell pellet was rinsed with FCC-M medium containing neither yeast extract nor any other inorganic or organic nitrogen source. During the culture, three additions of addition solution 1 were carried out, as well as additions of solution 2 in order to maintain glucose concentrations between 200 mM and 500 mM.

Culture Monitoring:

The total biomass concentration was monitored by measuring the dry mass (filtering on a Whatman GF/F filter and then drying in an oven at 105° C. for at least 24 hours before weighing).

The contents of total lipids and FAMEs were analyzed according to the methods classically described in the literature [Folch J, et al., A simple method for the isolation and purification of total lipids from animal tissues. *J Biol Chem*. 1957 May; 226(1):497-509].

Example 4

Culture in a Fermentor

The *Aurantiochytrium* cultures were prepared in fermentors, in a way similar to that described in Example 3. The procedure was modified with regard to the pH adjustment method by adding ammonia ($NH_4OH$) in order to avoid the significant $Na^+$ or $K^+$ supply associated with pH adjustment using NaOH or KOH, which could have made the valorization of the coproducts for animal feed more difficult. Part of the nitrogen needed for cell culture being supplied via the adjustment of pH with ammonia ($NH_4OH$), it was thus no longer necessary to include $(NH_4)_2SO_4$ in the composition of addition solution 1.

Table 3 presents the results of this example:

|  | Dry Matter (g/L) | DM Productivity (g/L/h) | Fat/DM (%) | DHA/Fat (%) | DHA (g/L) |
| --- | --- | --- | --- | --- | --- |
| CCAP 4062-1 FCC-M (KOH) | 129.2 | 1.83 | 40.75 | 31.92 | 16.81 |
| CCAP 4062-1 FCC-M | 127.9 | 1.67 | 50 | 32.6 | 20.85 |
| CCAP 4062-1 FCC-M ($NH_4OH$) | 120 | 1.566 | 35.09 | 38.01 | 16.01 |
| CCAP 4062-1 Instant Ocean ® | 131.5 | 1.85 | 49.9 | 23.00 | 15.09 |

The invention claimed is:

1. A method for producing DHA in a culture of protists of the genus *Aurantiochytrium* comprising the following step:
   a) culturing, in heterotrophic or mixotrophic conditions, one or more strains of the genus *Aurantiochytrium* in a chemically defined culture medium,
   b) maintaining said culture for several generations, and
   c) recovering the biomass thus cultured,
   wherein
      the one or more strains of the genus *Aurantiochytrium* has a genetic identity of at least 92% to sequence SEQ ID NO: 1 and
      the chemically defined culture medium has less than 3.5 g/L of sodium ions and less than 1 g/L of chloride ions and has 200 mM to 500 mM organic carbon-containing substrate.

2. The method according to claim 1, wherein the strain of the genus *Aurantiochytrium* also has a genetic identity of at least 96% to sequence SEQ ID NO: 2, and/or at least 91% to sequence SEQ NO: 3 and/or at least 95% to sequence SEQ ID NO: 4.

3. The method according to claim 1, wherein the culture medium has less than 3.5 g/L of sodium ions and less than 200 mg/L of chloride ions.

4. The method of claim 3, wherein the culture medium has less than 1 g/L of sodium ions.

5. The method of claim 3, wherein the culture medium has less than 6 mg/L of sodium ions.

6. The method according to claim 1, wherein the medium does not contain an osmotic pressure regulatory agent.

7. The method according to claim 1, further comprising the steps of:
   d) recovering the lipids of the strains, and optionally,
   e) extracting the DHA (docosahexaenoic acid).

8. The method according to claim 1, wherein the culture medium consists of:

| Ingredients | Concentration |
|---|---|
| KCl | 0.05-5 g/L |
| $H_3BO_3$ | 0.01-0.3 g/L |
| $MgSO_4, 7H_2O$ | 2-10 g/L |
| $CaCl_2, 2H_2O$ | 0.2-0.9 g/L |
| $KNO_3$ | 0.01-0.06 g/L |
| $KH_2PO_4, 7H_2O$ | 0.2-1 g/L |
| $Na_2EDTA, 2H_2O$ | 0.001-0.005 g/L |
| $ZnSO_4 \cdot 7H_2O$ | 0.01-0.1 mg/L |
| $CoCl_2 \cdot 6H_2O$ | 0.01-0.1 mg/L |
| $MnCl_2 \cdot 4H_2O$ | 0.05-1 mg/L |
| $Na_2MoO_4, 2H_2O$ | 0.0005-0.1 mg/L |
| $Na_2SeO_3$ | 0.01-0.5 mg/L |
| $NiSO_4 \cdot 6H_2O$ | 0.5-5 mg/L |
| $CuSO_4 \cdot 5H_2O$ | 0.0025-1 mg/L |
| EDTA—Fe | 10-50 mg/L |
| Glucose | 20-60 g/L |
| $(NH_4)_2SO_4$ | 2-9 g/L |
| Thiamine | 1-50 mg/L |
| Vitamin B12 | 0.025-5 mg/L |
| Pantothenate | 0.1-25 mg/L. |

9. The method according to claim 1, wherein the biomass derived from step b) represents at least 100 g/L of dry matter.

10. The method according to claim 1, wherein the DHA concentration at the conclusion of step b) represents at least 15 g/L.

11. The method according to claim 1, wherein the DHA contained in the biomass at the conclusion of step b) represents more than 30% of the total lipids.

12. The method according to claim 1, wherein it has a DHA productivity of at least 0.1 g/L/h.

13. The method according claim 1, wherein said organism of the genus *Aurantiochytrium* corresponds to strain FCC 1324, deposited with the CCAP (Culture Collection of Algae and Protozoa), under accession number CCAP 4062/1.

14. The method according to claim 1, wherein the medium does not contain an osmotic pressure regulatory agent selected among the group consisting of mannitol, sorbitol, polyethylene glycol and sucrose.

* * * * *